(12) United States Patent
Johns et al.

(10) Patent No.: US 10,730,018 B2
(45) Date of Patent: Aug. 4, 2020

(54) MASS EXCHANGE APPARATUS AND METHODS FOR THE USE THEREOF

(71) Applicant: Haemair Limited, Singleton Park (GB)

(72) Inventors: William R. Johns, Singleton Park (GB); Alan F. Evans, Singleton Park (GB); Ronald K. Knight, Singleton Park (GB)

(73) Assignee: Haemair Limited, Singleton Park, SA (GB)

( * ) Notice: Subject to any disclaimer, the term of this patent is extended or adjusted under 35 U.S.C. 154(b) by 328 days.

(21) Appl. No.: 15/546,535

(22) PCT Filed: Jan. 18, 2016

(86) PCT No.: PCT/GB2016/050098
§ 371 (c)(1),
(2) Date: Jul. 26, 2017

(87) PCT Pub. No.: WO2016/120591
PCT Pub. Date: Aug. 4, 2016

(65) Prior Publication Data
US 2018/0015419 A1    Jan. 18, 2018

(30) Foreign Application Priority Data
Jan. 28, 2015    (GB) .................................. 1501411.1

(51) Int. Cl.
*B01D 37/00*    (2006.01)
*B01D 61/32*    (2006.01)
(Continued)

(52) U.S. Cl.
CPC ........... *B01D 61/32* (2013.01); *A61M 1/1631* (2014.02); *A61M 1/1698* (2013.01); *B01D 63/02* (2013.01);
(Continued)

(58) Field of Classification Search
CPC ........ B01D 37/00; B01D 39/00; B01D 43/00; B01D 61/00; B01D 61/28; B01D 2201/30;
(Continued)

(56) References Cited

U.S. PATENT DOCUMENTS 3,771,658 A    11/1973 Brumfield
3,834,544 A    9/1974 Tyson et al.
(Continued)

FOREIGN PATENT DOCUMENTS

EP    0003495 A1    8/1979
JP    06237992 A    8/1994
(Continued)

OTHER PUBLICATIONS

International Preliminary Report on Patentability from International Application No. PCT/GB2016/050098, dated Aug. 10, 2017, 8 pages.
(Continued)

*Primary Examiner* — Allison G Fitzsimmons
(74) *Attorney, Agent, or Firm* — Shumaker & Sieffert, P.A.

(57) ABSTRACT

There is described a method of use of a mass exchanger. In the method the mass exchanger comprises: a first channel for accommodating flow of a liquid to be treated; and a second channel for accommodating flow of a treatment agent, the first and second channels have a permeable membrane provided between them, so as to allow transfer of selected species between the first channel and the second channel. The steps of the mass transfer method comprise passing the liquid to be treated along the first channel and introducing a mixture of liquid and gas into the second channel to provide a two-phase treatment agent. It is desirable to provide a means of adjusting the concentration of gas species in a
(Continued)

liquid such as blood, while simultaneously controlling the temperature of the liquid and optionally adjusting the concentration of ionic and/or dissolved species in that liquid. By this method and mass exchanger providing a two-phase treatment agent, it is possible to simultaneously deliver gaseous species (e.g. oxygen) into the treated liquid, while making use of the high heat capacity of the liquid phase of the treatment agent to transfer significant heat into or from the treated liquid.

13 Claims, 2 Drawing Sheets

(51) Int. Cl.
*A61M 1/16* (2006.01)
*B01D 63/08* (2006.01)
*B01D 63/02* (2006.01)
*B01D 39/00* (2006.01)

(52) U.S. Cl.
CPC ......... *B01D 63/08* (2013.01); *A61M 2205/36* (2013.01); *B01D 2311/10* (2013.01); *B01D 2313/38* (2013.01)

(58) Field of Classification Search
CPC .... B01D 63/00; B01D 63/06; B01D 2311/00; B01D 2311/02; B01D 2311/04; A61M 1/03; A61M 1/1698; A61M 1/16; A61M 1/02; A61M 1/0281; A61M 1/04; A61M 1/34; A61M 1/36
USPC ........... 422/44, 45, 46; 604/6.13, 6.14, 6.09; 210/321.6, 321.72, 323.1, 500.21; 55/350.1, 418, 419, 421
See application file for complete search history.

(56) References Cited

U.S. PATENT DOCUMENTS

| | | |
|---|---|---|
| 5,614,378 A | 3/1997 | Yang et al. |
| 2008/0014115 A1* | 1/2008 | Johns ................ A61M 1/1678 422/46 |
| 2009/0018484 A1 | 1/2009 | Levitov |
| 2011/0268609 A1 | 11/2011 | Reggiani |

FOREIGN PATENT DOCUMENTS

| | | |
|---|---|---|
| JP | 06237993 A | 8/1994 |
| WO | 2005097969 A1 | 10/2005 |
| WO | 2009098457 A2 | 8/2009 |

OTHER PUBLICATIONS

Search Report under Section 17(5) dated Jun. 23, 2015 in counterpart GB Application No. 1501411.1, 4 pps.
International Search Report and the Written Opinion dated May 10, 2016 in counterpart International Application PCT/GB2016/050098, 13 pps.
Communication pursuant to Article 94(3) EPC for corresponding European Patent Application No. 16702973.5 dated Dec. 18, 2018, 7 pgs.
The Second Office Action for corresponding CN Application No. 201680011432.X, dated Dec. 17, 2019, 8 pgs.

\* cited by examiner

MASS EXCHANGE APPARATUS AND METHODS FOR THE USE THEREOF

This application is a U.S. national phase application under 37 U.S.C. § 371 of international application number PCT/GB2016/050098 filed on Jan. 18, 2016, which claims the benefit of priority to GB application number 1501411.1 filed Jan. 28, 2015. The entire contents of each of international application number PCT/GB2016/050098 and GB application number 1501411.1 are incorporated herein by reference.

The present invention relates to mass exchange apparatus and methods for the use thereof, in particular to mass exchange apparatus for modifying the composition and temperature of liquid samples.

There are a variety of circumstances in which it is desirable to alter the properties of blood (or blood products, such as packed cells). These circumstances include blood transfusion, cardiopulmonary bypass (CPB), extracorporeal membrane oxygenation (ECMO) and kidney dialysis. The properties that may be changed include:

oxygen and carbon dioxide concentration (blood transfusion, CPB, ECMO)
temperature (blood transfusion, CPB, ECMO)
concentration of ions and dissolved species (blood transfusion, kidney dialysis, CPB, ECMO)

Currently these changes are made in separate stages.

In relation to temperature change, transfusion blood may be allowed to warm to room temperature or be warmed with a blood warmer before being administered to a patient. In other situations, blood may be cooled, for example, during operations such as cardiopulmonary bypass, in which patients are kept at a low temperature to slow down the metabolism. In Extracorporeal Membrane Oxygenation, blood may be cooled or heated, as required to maintain the patient at a desired temperature.

CPB and ECMO devices currently consist of two stages, a heat exchange stage followed by a mass exchange stage. The heat exchange stage follows conventional technology of either a tubular (e.g. hollow fibre) or plate and frame exchanger. Alternatives have been proposed in which heat and mass exchange are undertaken concurrently by interlaying permeable membranes for mass exchange and impermeable membranes for heat exchange (see, for example, U.S. Pat. No. 3,834,544).

Gas exchange can be undertaken through microporous or gas permeable membranes. Such exchange is desirable in blood transfusion (as well as in CPB and ECMO) so that blood is delivered to the patient at near arterial conditions (with high oxygen and low carbon dioxide) rather than venous conditions.

Ion and dissolved species exchange can be achieved through suitable microporous membranes. It is currently undertaken in dedicated mass exchangers for kidney dialysis. It is desirable also to adjust the ion and soluble species concentrations in transfusion blood to bring it nearer to fresh blood conditions. Specifically, it is desirable to recover near-fresh blood conditions for conventionally stored transfusion blood.

Adjusting and correcting the ion and soluble species concentrations is also desirable as an option in CPB and ECMO. Patients undergoing CPB and ECMO frequently have associated and concurrent health problems that can result in an accumulation of undesirable species and/or the depletion of desirable species in the blood. The ability to recover desirable concentrations of these species can aid patient recovery and reduce the risks to patient health and well being from these associated health problems.

Currently, heat transfer, gas transfer and transfer of soluble species can only be undertaken in series or by use of complex multi-layer exchangers (such as of U.S. Pat. No. 3,834,544).

It is desirable to provide a means of adjusting the concentration of gas species in a liquid such as blood, while simultaneously controlling the temperature of the liquid and optionally adjusting the concentration of ionic and/or dissolved species in that liquid.

Therefore, in a first aspect, the present invention may provide a method of use of a mass exchanger, wherein the mass exchanger comprises:

a first channel for accommodating flow of a liquid to be treated; and
a second channel for accommodating flow of a treatment agent,
the first and second channels having a permeable membrane provided therebetween, so as to allow transfer of selected species between the first channel and the second channel,
the method comprising the steps of passing the liquid to be treated along the first channel and introducing a mixture of liquid and gas into the second channel to provide a two-phase treatment agent.

By using a two-phase treatment agent, it is possible to simultaneously deliver gaseous species (e.g. oxygen) into the treated liquid, while making use of the high heat capacity of the liquid phase of the treatment agent to transfer significant heat into or from the treated liquid.

A further benefit of employing the two phase treatment agent is that with an aqueous transfer fluid microporous membranes may be employed in ECMO oxygenators. Use of microporous membranes in conventional ECMO oxygenators with blood/gas exchange has been avoided as in use the pores of the microporous membranes become blocked with protein. This results in the membranes having a useful maximum life of between 6 and 24 hours and less efficient membranes that do not have pores fully penetrating the thickness of the membrane have to be employed. An aqueous extraction fluid can reduce or eliminate pore blockage in microporous membranes. Consequently, more efficient microporous membranes can be used for ECMO applications. Such membranes also enable abnormal blood plasma composition to be corrected. Suitable treatment fluids can be designed to add deficient species, and/or to remove any undesirable species that may be present in the blood.

The present invention requires that both gas and liquid are introduced into the second channel and so is distinguished from processes in which a two-phase treatment agent is generated solely through a process of evaporation and/or condensation occurring within the second channel. With both gas and liquid introduced into the second channel the resulting 2-phase flow provides enhanced gas transfer with the benefit of a simpler and less expensive design. In addition the presence of the gaseous phase enhances mass transfer to and from the liquid phase in which it is mixed.

The present invention is also distinguished from processes in which the desired gas component is dissolved in the treatment liquid or bound to species suspended in the treatment liquid, and from processes such as scrubbing (absorption) and stripping (desorption). In scrubbing (absorption) and stripping (desorption) the primary purpose of the 2-phase gas/liquid mixture is to promote mass exchange between the two phases.

The treated liquid may be blood (e.g. whole blood or a blood product such as packed blood cells). In other examples, the treated liquid may be a microbial culture, as it is generally desirable to exercise close control over the temperature and composition of such cultures.

By means of the invention, it is possible to provide a relatively simple one-stage treatment of liquid (e.g. blood), such that the treated liquid follows a simple and short flow path through the mass exchanger. The simple path avoids the creation of areas of low flow or stagnation and the one-stage treatment reduces overall residence time of the liquid through the apparatus.

In applications where whole blood is used, such as CPB and ECMO, the resulting low residence time reduces the time available for blood to clot and hence reduces the risk of blood clots. Furthermore, the simple short flow path reduces the stress on the red blood cells and hence the tendency for haemolysis (this is also advantageous where the liquid to be treated is a blood product). Such simple short flow paths are also beneficial for other liquid mixtures, for example media to support microbial growth where the risk of growth of undesired microorganisms within the apparatus is reduced.

In certain cases, the liquid to be treated and the liquid phase of the treatment agent have different temperatures at the time of entry into the first and second channels respectively. Thus, for example, blood may be warmed to body temperature before being delivered to a patient. In other cases, the liquid phase of the treatment agent may have the same temperature as the treated liquid, so as to maintain the temperature of the treated liquid at the desired level. In yet other cases, the liquid phase of the treatment agent may have a temperature below body temperature.

In certain cases, the permeable membrane may be permeable to gas but impermeable to liquid. In other cases, the permeable membrane may be microporous, that is, it may allow passage of liquids and dissolved species across it (in addition to gases).

In certain cases, the treated liquid and the treatment agent flow in a counter-current relationship to each other. This arrangement may enhance both heat and mass transfer rates. In other arrangements, the flow may be co-current or cross-current.

In general, the mass exchanger is oriented such that the first and second channels extend in an upright direction.

In certain circumstances, the blood may flow downwards along the first channel. For example, in blood transfusion, a downwards flow facilitates delivery of blood from a conventional drip stand. Downward flow may also be desirable in ECMO and CPB to help ensure that any bubbles that may be present in the blood travel in an opposite direction to the blood flow, thereby avoiding the risk of bubbles exiting the mass exchanger with the blood and entering the patient's body. In other cases, an upwards flow may be desirable to purge bubbles from the apparatus, which are then removed by a bubble trap.

The permeable membrane may be provided e.g. in the form of a planar screen. In other cases, the second channel may have a tubular shape, its wall being provided by the permeable membrane.

Preferably the treatment agent is introduced to the mass exchanger through two inlet ports: a gas inlet port for the gas phase and a liquid inlet port for the liquid phase. The two ports are separately in fluid communication with a mixing chamber, the mixing chamber being in fluid communication with the second channel. The two phases mix in the mixing chamber and pass through the second channel of the mass exchanger. Preferably, the gas inlet is located upstream of the liquid inlet in order to promote good mixing.

Preferably, following its passage through the second channel, the treatment agent is introduced into a separation chamber provided downstream of the mass exchanger. In the separation chamber, the two phases of the two-phase treatment agent are caused to separate out, for example, through the action of gravity. The separation chamber may comprise two outlets, each outlet being for discharging flow of a respective phase of the two-phase treatment agent.

In certain embodiments, the liquid phase of the two-phase treatment agent may be reconditioned after its passage through the mass exchanger, for example, by means of an ion exchanger, such as an ion exchange resin. This procedure may allow any changes effected to the composition of the liquid phase during its passage through the mass exchanger to be at least partly reversed. This may allow the liquid phase to be recycled.

Reconditioning of the liquid phase of the two-phase treatment agent may be carried out before or after separation of the two phases of the two-phase treatment agent. Preferably, this procedure is carried out after separation of the liquid phase from the gas phase.

In a second aspect, the present invention may provide a mass exchanger for use in a method according to the first aspect of the invention, the mass exchanger comprising:
  a first channel for accommodating flow of a liquid to be treated; and
  a second channel for accommodating flow of a treatment agent,
  the first and second channels having a permeable membrane provided therebetween, so as to allow transfer of selected species between the first channel and the second channel,
  wherein the mass exchanger further comprises a gas delivery duct and a liquid delivery duct, both delivery ducts being in fluid communication with the second channel, wherein one or both of the gas and liquid delivery ducts is provided with a permeable wall extending across its cross-section, the permeable wall acting to promote even distribution of fluid across the cross-section of the duct.

In an embodiment, the present invention may provide a mass exchanger, the mass exchanger having an exchange region comprising:
  the first channel for accommodating flow of a liquid to be treated; and
  the second channel for accommodating flow of a treatment agent,
  the first and second channels having a permeable membrane provided therebetween, so as to allow transfer of selected species between the first channel and the second channel,
  wherein a mixing chamber is provided upstream of the exchange region, the mixing chamber being configured to receive fluid flow from a liquid inlet and a gas inlet,
  the mixing chamber being provided with at least one partition, the partition being oriented along a direction leading from the mixing chamber into the exchange region.

In an embodiment, the present invention may provide a mass exchanger comprising:
  the first channel for accommodating flow of a liquid to be treated; and
  the second channel for accommodating flow of a treatment agent,
  the first and second channels having a permeable membrane provided therebetween, so as to allow transfer of selected species between the first channel and the second channel, the second channel comprising at least one partition oriented laterally to the permeable membrane along the direction of flow of fluid through the channel.

Effectively, the present invention allows for the simultaneous independent control of the transfer of heat and/or gas and/or dissolved species. Thus, it contrasts with known multi-phase combined heat and mass transfer operations in which the heat of phase change is significant and the transfer processes are linked (such as evaporation, condensation and perfusion).

The invention will now be described by way of example with reference to the following Figures in which.

Figure 1:
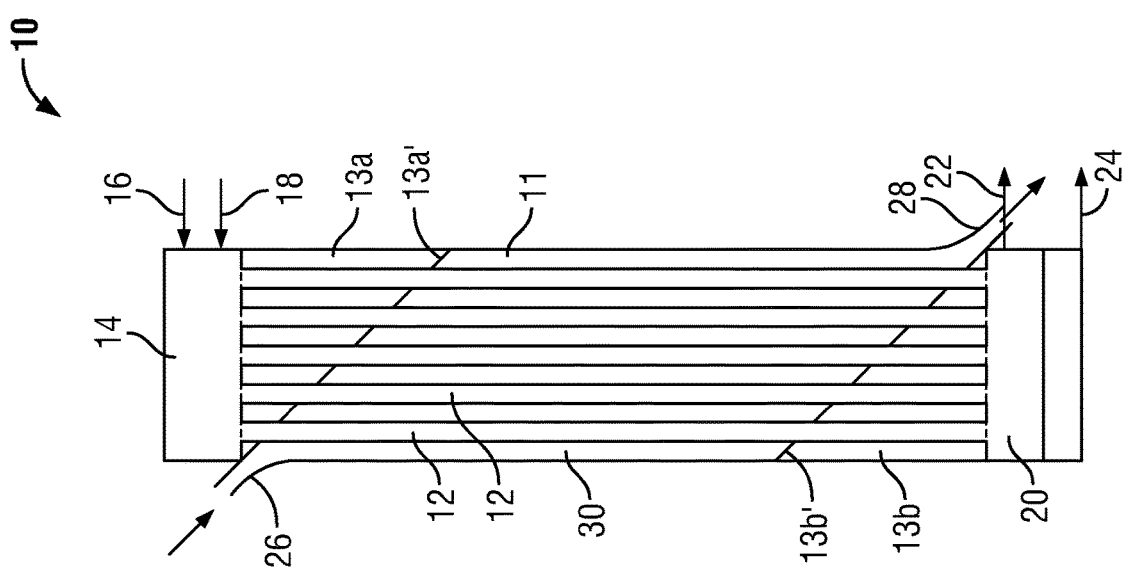
FIG. 1 shows a schematic cross-sectional view of a first mass exchanger for use in the method of the first aspect of the invention.

Referring to FIG. 1, a mass exchanger 10 comprises a housing 11 and a plurality of tubular ducts 12 located within the housing 11. The tubular ducts 12 are in a spaced relationship in alignment with each other, and are held in place by resin blocks 13a,b disposed within the housing 11 at the upstream and downstream ends of the ducts. The resin blocks have free surfaces 13a' and 13b' that are oriented at an oblique angle to the ducts 12.

The walls of the tubular ducts are permeable to gas and optionally ionic species (for example, the walls may be provided by gas permeable but liquid impermeable materials such as polymethylpentene or polyphenylene oxide. Alternatively, the walls may be microporous and hence permeable to small molecules, including gases, liquids, dissolved species and ionic species). A mixing chamber 14 is provided upstream of the tubular ducts 12 and is in fluid communication with the ducts. The mixing chamber 14 is arranged to receive gas flow from a gas inlet 16 and a liquid inlet 18. The gas inlet 16 is positioned upstream of the liquid inlet 18 (relative to the direction of flow of the gas and liquid through the tubular ducts). A separation chamber 20 is provided downstream of the tubular ducts 12 and is in fluid communication with the ducts. The separation chamber includes a gas outlet 22 and a liquid outlet 24, the liquid outlet being downstream of the gas outlet (relative to the flow of gas and liquid through the tubular ducts).

The housing 11 has a blood inlet 26 and a blood outlet 28. The inlet and outlet 26,28 are in fluid communication with an interior volume 30 of the housing, the interior volume 30 being bounded by the interior walls of the housing 11, the external surface of the ducts 12 and the free surfaces of the resin blocks 13a, 13b. The orientation of the free surfaces of the blocks 13a,b helps to ensure that blood is able to travel smoothly through the interior volume of the housing, without sudden changes in direction, and helps to avoid the formation of areas (e.g. adjacent to the main stream of blood flow) in which the blood may recirculate and stagnate, resulting in a residence time that is sufficient for clotting of the blood to occur.

In use, the mass exchanger 10 is oriented such that the tubular ducts 12 extend in an upright direction. Blood (such as whole blood or a blood product) is caused to flow through the interior volume 30 of the housing 11, from the blood inlet 26 to the blood outlet 28. At the same time, a two-phase treatment fluid comprising liquid and gas phases is caused to flow along the tubular ducts 12 from the mixing chamber 14 to the separation chamber 20. Migration of species across the permeable walls of the ducts 12 allows the composition of the blood to be adjusted as required. For example, the gas phase may comprise predominantly oxygen, to oxygenate the blood and/or remove carbon dioxide from the blood. The gas phase may also contain a controlled concentration of carbon dioxide to avoid excessively low concentrations of carbon dioxide in the blood and/or may contain a small carefully controlled concentration of nitric oxide to alleviate any deficiency of nitric oxide in the blood.

Furthermore, where the walls of the tubular ducts comprise microporous membranes, the concentration of certain ionic species in the liquid phase (e.g. potassium and/or iron) may be held at a low level to reduce the concentrations of these species in the blood. The liquid phase may also contain components with an affinity for such species whose concentrations it is desired to reduce. The liquid phase may also contain concentrations of species that it is desired to transfer into the blood.

Furthermore, the temperature of the liquid may be selected so as to promote heat transfer to or from the blood, such that the temperature of the blood is adjusted as required. For example, the temperature of the liquid phase may be selected so as to bring the blood to near body temperature.

The gas phase of the two-phase treatment fluid enters the mixing chamber 14 through the gas inlet 16, while the liquid phase of the treatment fluid enters the mixing chamber 14 through the liquid inlet 18. The gas and liquid mix flows downwards through the tubular ducts 12 driven by the respective supply pressures. Where a duct is low in liquid, there is less resistance to gas flow, and thus gas flows faster into the duct. This faster flow draws in liquid from the mixing chamber 14 into that duct, so as to correct the uneven distribution. This helps to ensure a reasonably uniform distribution of gas and liquid within each duct 12.

The gas and liquid phases separate in the separation chamber 20. The liquid phase is withdrawn through the liquid outlet 24 and the gas phase is withdrawn through the gas outlet 22.

In the embodiment of FIG. 1, the treatment fluid flows vertically downwards through the mass exchanger. In other embodiments, the treatment fluid may flow vertically upwards through the mass exchanger, a reasonably uniform distribution of gas and liquid through each duct being achieved through an analogous mechanism to the embodiment of FIG. 1.

In the embodiment of FIG. 1, the blood flows through the mass exchanger in the same direction as the treatment fluid. This arrangement is termed co-current flow. However, counter-current flow is also possible, where the blood and the treatment fluid flow in opposing directions through the mass exchanger.

As an alternative to separate gas and liquid inlets, the two-phase treatment fluid may be delivered to the mass exchanger as a pre-formed gas/liquid mixture.

Figure 2:
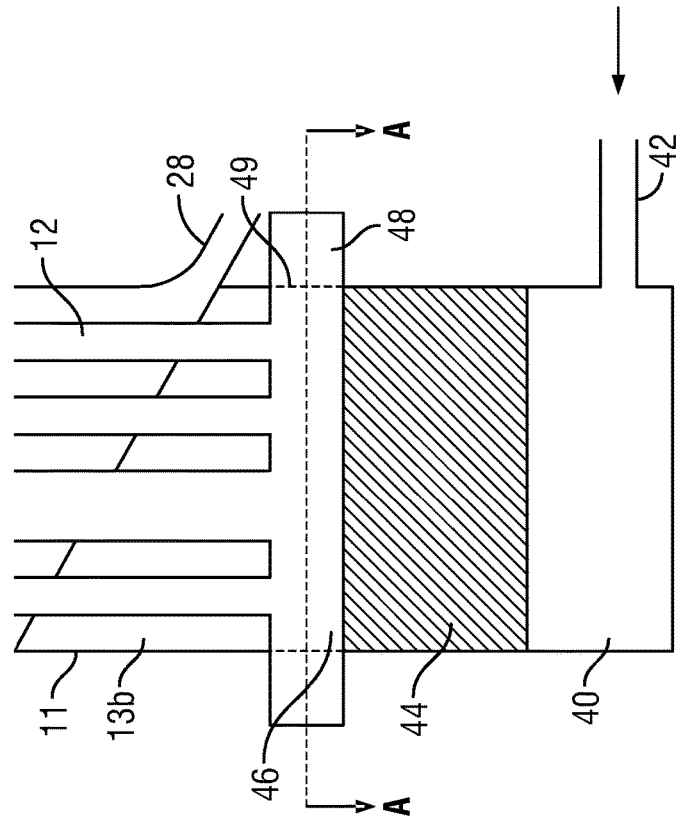
FIG. 2 shows a schematic cross-sectional view of a portion of a second mass exchanger for use in the method of the first aspect of the invention.

Referring to FIG. 2, a variant of the mass exchanger of FIG. 1 comprises a housing 11, tubular ducts 12, a resin block 13b and blood outlet 28 that all correspond to the equivalent features of FIG. 1.

The embodiment of FIG. 2 is configured such that the treatment fluid flows upwardly through the mass exchanger, that is, in counter-current flow relative to the blood. In alternative embodiments, the mass exchanger of FIG. 2 may be inverted, such that the treatment fluid flows downwardly through the mass exchanger.

A gas supply chamber 40 is provided upstream of the tubular ducts 12 and is provided with a gas inlet 42. The gas supply chamber is in fluid communication with the tubular ducts 12 via a porous block 44 and a liquid supply chamber 46 that is located adjacent to the tubular ducts 12. The liquid supply chamber 46 is provided with a liquid inlet 48. The liquid inlet 48 is in fluid communication with the liquid supply chamber via a permeable wall 49.

Figure 3:
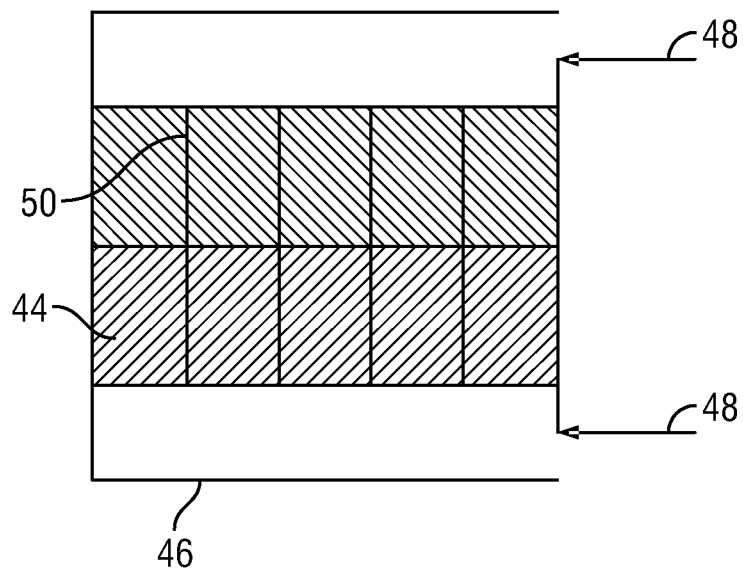
FIG. 3 shows a view of the mass exchanger of FIG. 2, taken along the line A-A.

Referring to FIG. 3, the liquid supply chamber 46 is provided with partitions 50 that are aligned with the flow axis of the mass exchanger.

In use, gas flows into the gas supply chamber 40 via gas inlet 42, and then proceeds to flow through porous block 44 into the liquid supply chamber 46. The provision of the porous block helps to ensure a reasonably uniform distribution of the gas across the cross-section of the mass exchanger as it enters the liquid supply chamber 46.

The liquid supply chamber contains liquid that is supplied from the liquid supply inlet 48 via the permeable wall 49. The provision of the permeable wall helps to ensure that the supply of liquid into the liquid supply chamber 46 is distributed reasonably uniformly across the width of the inlet 48.

The liquid entering the liquid supply chamber 46 mixes with the gas to provide a two-phase treatment fluid that flows into the tubular ducts 12. Partitions 50 in the liquid supply chamber help to maintain an even distribution of gas and liquid in the two-phase fluid by limiting the extent to which the gas and liquid phases can become separated in the liquid supply chamber e.g. if the mass exchanger is tilted.

Figure 4:
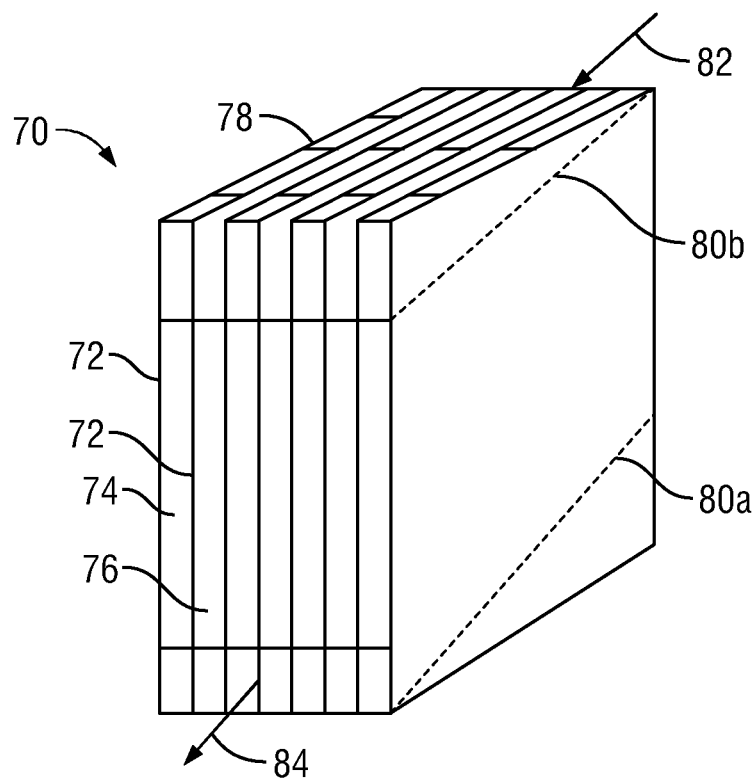
FIG. 4 shows a schematic perspective view of a portion of a third mass exchanger for use in the method of the first aspect of the invention.

Referring to FIG. 4, a mass exchanger 70 comprises a plurality of permeable screens 72 that are in a spaced relationship in alignment with each other. Adjacent pairs of permeable screens define flow channels therebetween, such that a series of treatment fluid channels 74 are provided, the treatment fluid channels alternating with blood channels 76.

The treatment fluid channels 74 each comprise multiple partitions 78 that extend across each respective channel, between the respective screens of that channel. Thus, each treatment fluid channel comprises multiple sub-channels. The sub-channels extend along a longitudinal axis of the mass exchanger.

The blood channels extend generally along a transverse direction of the mass exchanger, each channel being bounded by a respective pair of screens and a pair of shaping elements 80a,b that are oriented obliquely to the longitudinal axis of the mass exchanger. The shaping elements 80a,b help to ensure that blood flows smoothly from a blood inlet 82 to a blood outlet 84, the inlet and outlet being disposed on opposite sides of the mass exchanger.

The treatment fluid is introduced into the treatment fluid channels by means of one or more mixing chambers, supply chambers, and/or fluid inlets, such as described in relation to FIGS. 1 and 2. The partitions 78 within the treatment fluid channels help to limit the extent to which the gas and liquid phases become separated if the mass exchanger is tilted.

In a variant of the embodiment shown in FIG. 4, the blood channels and the treatment fluid channels may both extend along a longitudinal axis of the mass exchanger. In this case, the blood inlet and outlet are located at the upstream and downstream ends of the mass exchanger and no additional shaping elements are required. The invention envisages and encompasses the employment of alternative means of achieving near uniform gas/liquid mixtures in all channels such as will be apparent to those skilled in the art.

The invention claimed is:

1. A method of use of a mass exchanger, the method comprising:
    passing a liquid to be treated along a first channel of the mass exchanger, wherein the mass exchanger comprises the first channel configured to accommodate flow of a liquid to be treated and a second channel configured to accommodate flow of a treatment agent; and
    introducing a mixture of liquid and gas into the second channel to provide a two-phase treatment agent, wherein the first and second channels have a microporous permeable membrane therebetween so as to allow simultaneous transfer of selected gas and selected dissolved species between the first channel and the second channel.

2. The method according to claim 1, wherein the liquid to be treated is blood.

3. The method according to claim 1, wherein the liquid to be treated is a liquid microbial culture.

4. The method according to claim 1, wherein the liquid to be treated is a blood product.

5. The method according to claim 1, wherein the liquid to be treated and the liquid phase of the two-phase treatment agent have different temperatures at the time of entry into the first and second channels, respectively.

6. The method according to claim 1, wherein the composition of the liquid phase of the two-phase treatment agent is such that the selected dissolved species are caused to migrate across the microporous permeable membrane between the liquid to be treated and the two-phase treatment agent.

7. The method according to claim 1, wherein the permeable membrane is provided in the form of a planar screen.

8. The method according to claim 1, wherein the second channel has a tubular shape.

9. The method according to claim 1, wherein the mass exchanger is oriented such that the first and second channels extend in an upright direction.

10. The method according to claim 9, wherein the liquid to be treated is passed in an upwards direction along the first channel.

11. The method according to claim 9, wherein the liquid to be treated is passed in a downwards direction along the first channel.

12. The method according to claim 1, wherein the mass exchanger comprises a gas inlet and a liquid inlet that are separately in fluid communication with a mixing chamber, the mixing chamber being in fluid communication with the second channel, wherein the gas inlet is located upstream of the liquid inlet, and the gas phase of the two-phase treatment agent is introduced into the gas inlet and the liquid phase of the two-phase treatment agent is introduced into the liquid inlet.

13. The method according to claim 1, wherein subsequently to the passage of the two-phase treatment agent through the mass exchanger, the liquid phase of the two-phase treatment agent is reconditioned to reverse at least in part any compositional changes that have occurred in the liquid phase during passage of the two-phase treatment agent through the mass exchanger.

* * * * *